US006944895B2

(12) United States Patent
Truwit

(10) Patent No.: US 6,944,895 B2
(45) Date of Patent: Sep. 20, 2005

(54) INTERVENTIONAL MR SURGICAL TABLE

(75) Inventor: Charles L. Truwit, Wayzata, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 10/260,697

(22) Filed: Sep. 30, 2002

(65) Prior Publication Data

US 2003/0079287 A1 May 1, 2003

Related U.S. Application Data

(63) Continuation-in-part of application No. 09/849,792, filed on May 4, 2001, now abandoned.
(60) Provisional application No. 60/202,358, filed on May 5, 2000.

(51) Int. Cl.[7] .......................... A61G 13/04; A61G 13/12
(52) U.S. Cl. .............................. 5/601; 5/607; 378/209; 600/415; 600/410
(58) Field of Search ............................ 5/601, 607, 600, 5/608, 609; 378/209, 208; 600/415, 410, 425; 324/318

(56) References Cited

U.S. PATENT DOCUMENTS

| | | | | |
|---|---|---|---|---|
| 3,609,357 A | * | 9/1971 | Jones .............................. | 5/601 |
| 4,771,785 A | * | 9/1988 | Duer .............................. | 5/601 |
| 5,152,024 A | * | 10/1992 | Chrones et al. ................. | 5/609 |
| 5,207,224 A | | 5/1993 | Dickinson et al. ........ | 128/653.5 |
| 5,272,776 A | | 12/1993 | Kitamura ....................... | 5/81.1 |
| 5,305,749 A | | 4/1994 | Li et al. ................... | 128/653.2 |
| 6,195,578 B1 | | 2/2001 | Distler et al. ................ | 600/415 |
| 6,201,394 B1 | * | 3/2001 | Danby et al. ................ | 324/319 |
| 6,249,695 B1 | * | 6/2001 | Damadian ....................... | 5/607 |

FOREIGN PATENT DOCUMENTS

AU 210169 * 10/1957 ..................... 5/609

* cited by examiner

*Primary Examiner*—Alexander Grosz
(74) *Attorney, Agent, or Firm*—Schwegman, Lundberg, Woessner & Kluth, P.A.

(57) ABSTRACT

There is described method and apparatus for supporting a patient's body in a MR scanner, including supporting it to rotate about its longitudinal axis and cant about a point on the longitudinal axis. Also provided are method and apparatus for supporting a patient's head and neck and using a surgical head-holder. Yet another embodiment of the invention provides method and apparatus for attaching first and second stirrups to a member supporting the patient. According to yet another embodiment, the invention provides for keeping two or more different members for supporting a patient's body during a medical procedure conducted in conjunction with an MR scanner, wherein each member is adapted to be detachably inserted into a bore of the MR scanner, and wherein each member provides for a different patient support functionality, selecting one of the different members for use in a medical procedure, positioning a patient's body on the selected member, and engaging the member with the MR scanner such that the member is disposed at least in part in a bore of the scanner.

7 Claims, 15 Drawing Sheets

INTERVENTIONAL MR SURGICAL TABLE

RELATED APPLICATION

This application is a continuation-in-part of U.S. patent application Ser. No. 09/849,792, filed May 4, 2001, now abandoned which claims benefit under 35 U.S.C. 119(e) from U.S. Provisional Application Ser. No. 60/202,358, filed May 5, 2000, which is incorporated by reference.

TECHNICAL FIELD OF THE INVENTION

The present invention relates generally to the field of medicine, and more particularly to MR scanning equipment and its use in medical procedures.

BACKGROUND

Since its development in the early 1980s, magnetic resonance (MR) imaging has become the dominant form in imaging of the central nervous systems and is continuing to grow in its uses in musculoskeletal and body imaging. It offers unprecedented abilities in visualization of the human body. Over the past few years, MR imaging has been investigated as a tool for use in association with therapy, so-called interventional MR imaging or MR-guided therapy. To accomplish this, various new scanner designs have been developed to permit surgical access to patients while inside the scanners. This has resulted in both more open MR scanners and new surgical tools that can be operated safely within the MR environment. Initially, new designs of the interventional MR suites have been required in order to permit surgical procedures in the MR environment. However, these designs have been first efforts and have not been optimized for both surgical procedures and clinical scanning. Specifically, new MR tables have been required with combined MR and surgical capabilities.

SUMMARY OF THE INVENTION

As described in more detail herein below, the present invention provides method and apparatus for supporting a patient's body on an elongate member with a substantially planar surface, the elongate member having a longitudinal axis, positioning the member inside a bore of a MR scanner so that at least a portion of the patient's body is inside the bore, and rotating the member about its longitudinal axis while the member is inside the bore, so that the patient's body is rotated about the body's longitudinal axis while in the bore of the MR scanner.

Also provided are method and apparatus for supporting a patient's body on an elongate member with a substantially planar surface, the elongate member having a longitudinal axis and a recess on one end substantially underneath the patient's head and neck and including a surgical head-holder supporting the patient's head above or within the recess and positioning the member inside a bore of a MR scanner so that at least a portion of the patient's body is inside the bore.

The invention further provides method and apparatus for supporting a patient's body on an elongate member with a substantially planar surface, the elongate member having a longitudinal axis, positioning the member inside a bore of a MR scanner so that at least a portion of the patient's body is inside the bore, and canting the member about a point along its longitudinal axis while the member is inside the bore, so that the head or feet of a patient may be raised or lowered with respect to one another while in the bore of the MR scanner.

According to yet another embodiment of the invention, there is provided a method and apparatus for supporting a patient's body on an elongate member with a substantially planar surface, the elongate member having a longitudinal axis, positioning the member inside a bore of a MR scanner so that at least a portion of the patient's body is inside the bore, and attaching first and second stirrups to the elongate member on one end and putting the feet of the patient in the stirrups.

According to yet another embodiment, the invention provides for keeping two or more different members for supporting a patient's body during a medical procedure conducted in conjunction with an MR scanner, wherein each member is adapted to be detachably inserted into a bore of the MR scanner, and wherein each member provides for a different patient support functionality, selecting one of the different members for use in a medical procedure, positioning a patient's body on the selected member, and engaging the member with the MR scanner such that the member is disposed at least in part in a bore of the scanner.

DETAILED DESCRIPTION OF THE INVENTION

Figure 1:
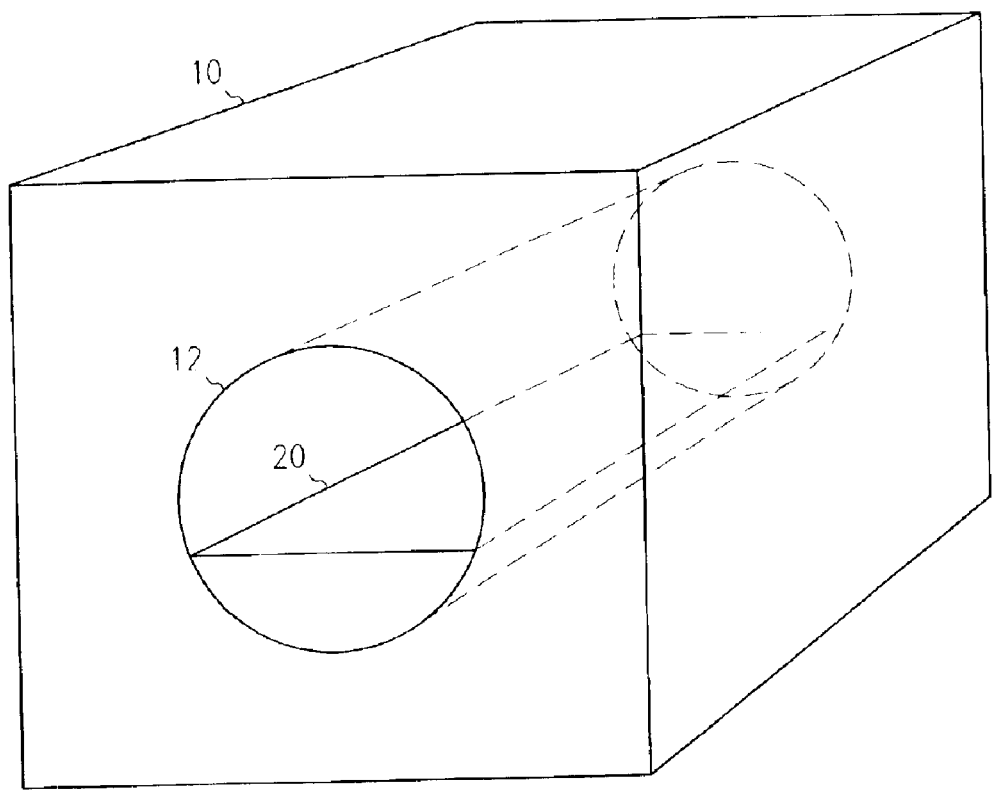
FIG. 1 illustrates an MR scanner of a type useful with the method and apparatus of the present invention.

In the following detailed description of the invention reference is made to the accompanying drawings which form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention.

Referring now to FIG. 1, there is illustrated in simplified form an example embodiment of a MR scanner 10 of the kind the methods and apparatus of the present invention can be used with. Scanner 10 has a bore 12 within which a patient is supported on a surface of member 20 and MR scans of the patient's body may be performed. Various example embodiments of the methods and apparatus of the present invention are described below.

Figure 2:
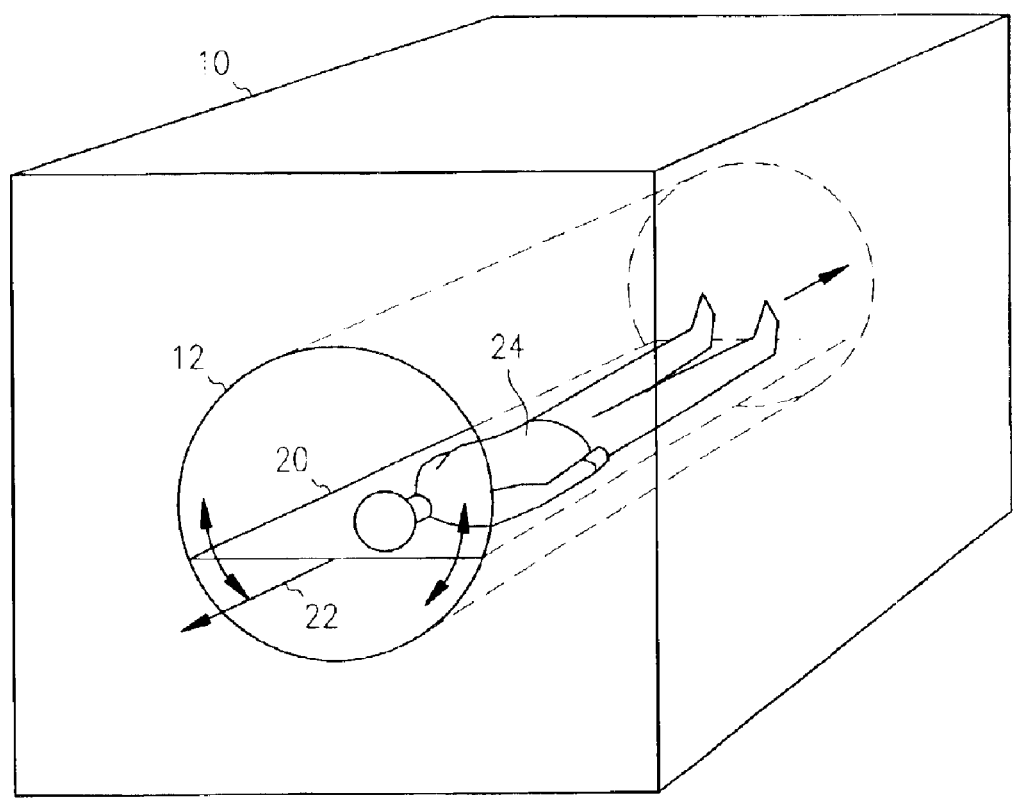
FIG. 2 illustrates a first embodiment of a method and apparatus according to the present invention wherein a patient's body is rotated about its longitudinal axis.

Referring now to FIG. 2, there is illustrated a first embodiment of a method and apparatus according to the present invention. According to this embodiment, a patient's body 24 is supported on the elongate member 20 with a substantially planar surface, with the elongate member 20 having a longitudinal axis 22. The member 20 is positioned inside the bore 12 of MR scanner 10 so that at least a portion of the patient's body 24 is inside the bore 12. The member 20 is rotated about its longitudinal axis while the member is inside the bore 12, so that the patient's body 24 is rotated about the body's longitudinal axis 22 while in the bore 12 of the MR scanner. According to one embodiment, the member 20 is supported in the bore 12 on a mechanism (not shown) that supports the member 20 for rotation about the longitudinal axis 22. Such support may be provided on the edges of the member 20 or along one or more points across the center. Further, the member 20 is freely detachable from the mechanism and removable from the bore 12, for example onto a wheeled gurney.

Figure 3:
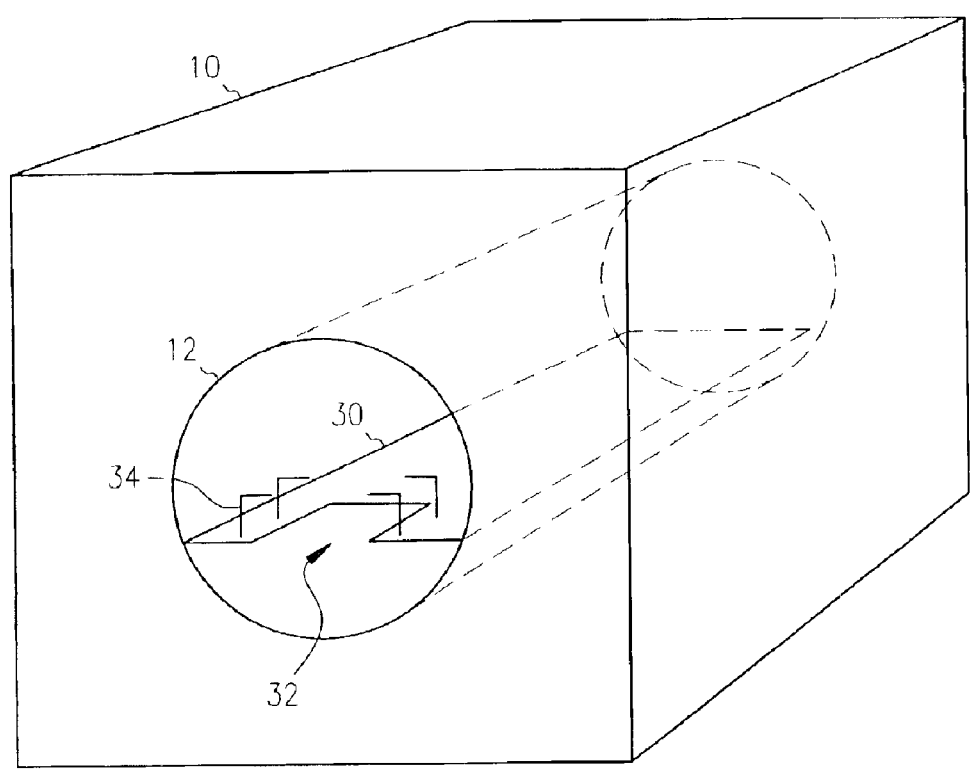
FIG. 3 illustrates a second embodiment of a method and apparatus according to the present invention wherein a patient's head is positioned using a surgical head-holder.

Referring now to FIG. 3, there is illustrated a second embodiment of a method and apparatus according to the present invention. According to this embodiment a patient's body is supported on an elongate member 30 with a substantially planar surface, the elongate member 30 having a longitudinal axis and a recess 32 on one end substantially underneath a patient's head and neck when lying on the table, and including a surgical head-holder 34 supporting the patient's head above or within the recess 32. The member 30 is positioned inside a bore 12 of a MR scanner 10 so that at least a portion of the patient's body is inside the bore 12. The member 30 is freely detachable from the mechanism and removable from the bore 12.

Figure 4:
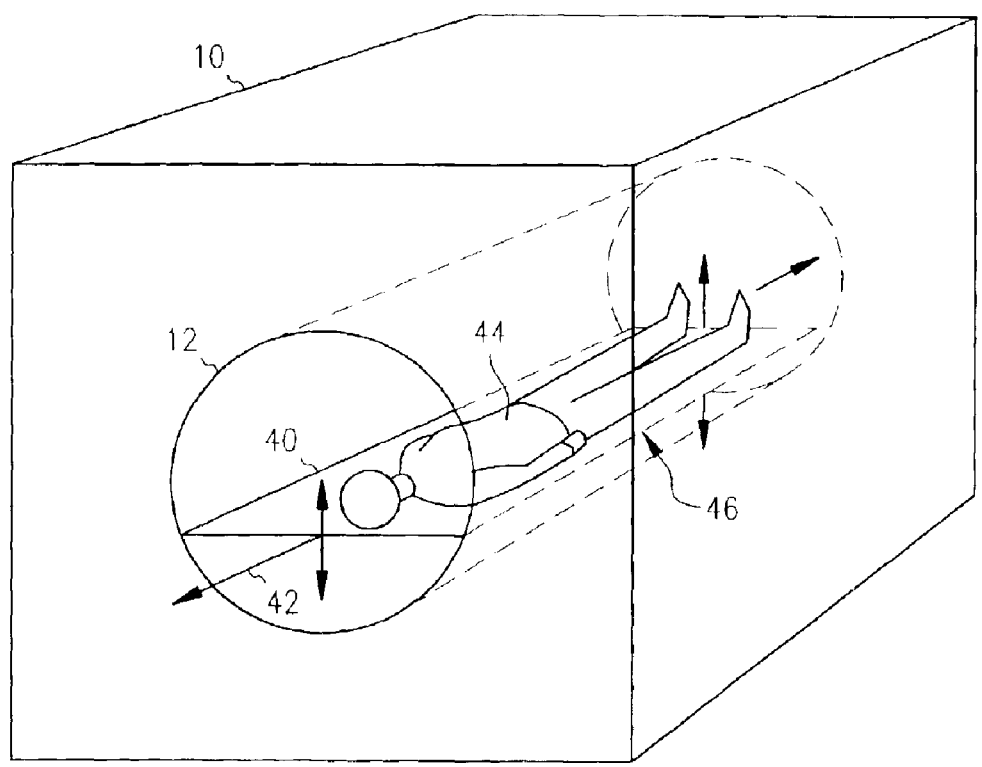
FIG. 4 illustrates yet another embodiment of a method and apparatus according to the present invention wherein a patient's body is canted about a point along its longitudinal axis.

Referring now to FIG. 4, there is illustrated yet another embodiment of a method and apparatus according to the present invention. A patient's body 44 is supported on an elongate member 40 with a substantially planar surface, the elongate member 40 having a longitudinal axis 42. The member 40 is positioned inside a bore 12 of a MR scanner 10 so that at least a portion of the patient's body 44 is inside the bore 12. The member 40 is canted about a point 46 along its longitudinal axis 42 while the member 40 is inside the bore 12, so that the head or feet of a patient 44 may be raised or lowered with respect to one another while in the bore 12 of the MR scanner 10. According to one example embodiment, the member 40 is supported in the bore 12 on a mechanism that supports the member 40 for canting. The member 40 may be canted using a hydraulically driven component. Further, according to one embodiment, the member 40 is freely detachable from the mechanism and removable from the bore 12.

Figure 5:
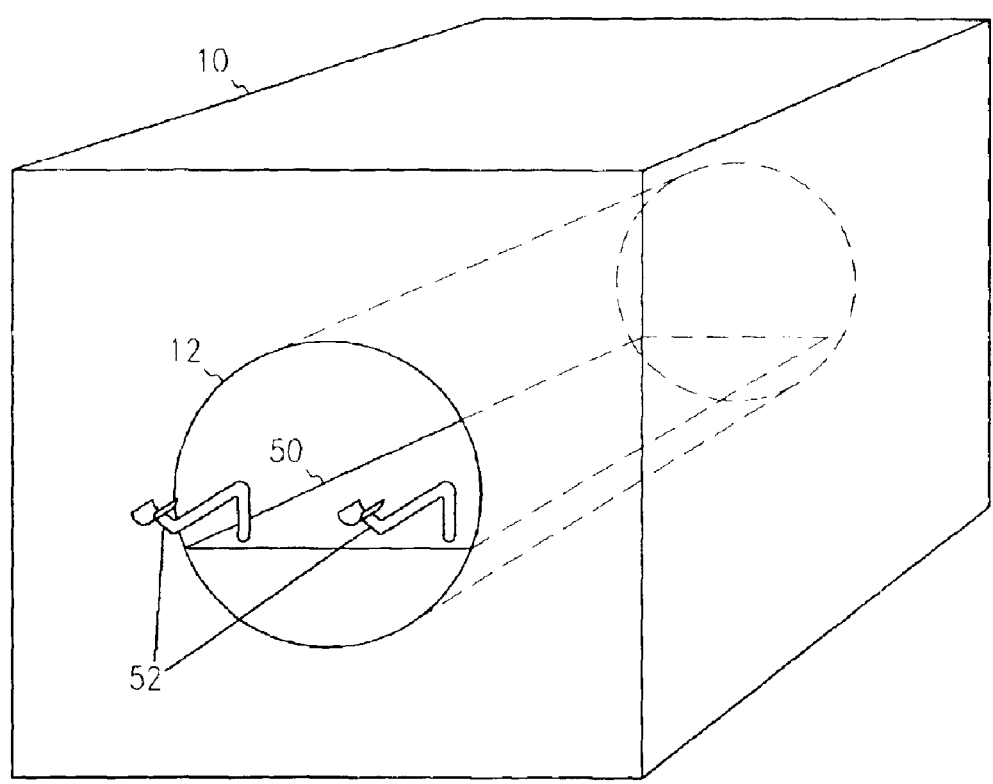
FIG. 5 illustrates yet another embodiment of a method and apparatus according to the present invention wherein stirrups are attached to the elongate member on one end.

Referring to FIG. 5, there is illustrated yet another embodiment of a method and apparatus according to the present invention. A patient's body is supported on an elongate member 50 with a substantially planar surface, the elongate member 50 having a longitudinal axis. The member 50 is positioned inside a bore 12 of a MR scanner 10 so that at least a portion of the patient's body is inside the bore 12 when supported on the member 50. First and second stirrups 52 are attached with a quick connect/disconnect mechanism to the elongate member 50 on one end and putting the feet of the patient in the stirrups 52. According to one example embodiment, the member 50 is freely detachable and removable from the bore 12.

Figure 6A:
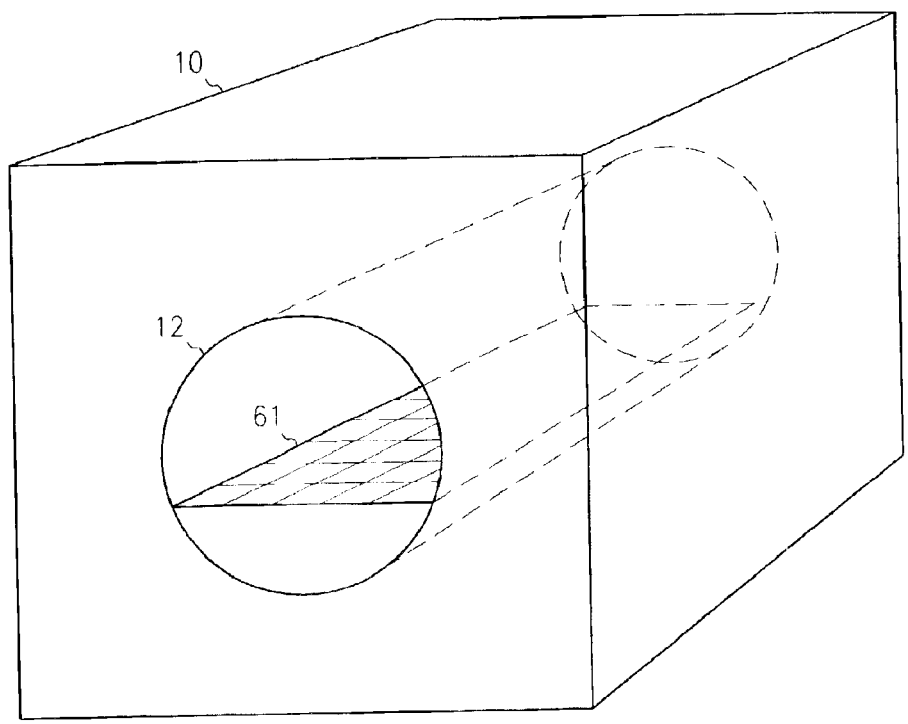
FIGS. 6A and 6B illustrate yet another embodiment of a method and apparatus according to the present invention wherein two or more different members are provided and kept for supporting a patient's body during a medical procedure conducted in conjunction with an MR scanner.
Figure 6B:
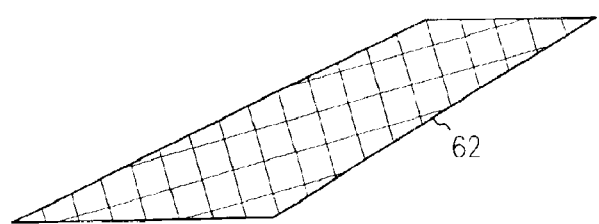

Referring to FIGS. 6A and 6B, there is illustrated yet further embodiments of a method and apparatus according to the present invention. Two or more different members 61 (inserted in bore 12) and 62 (not in use) are provided and kept for supporting a patient's body during a medical procedure conducted in conjunction with an MR scanner 10, wherein each member is adapted to be detachably inserted into a bore 12 of the MR scanner 10, and wherein each member provides for a different patient support functionality. One of the different members is selected for use in a medical procedure. The patient's body is positioned on the selected member, and the member is engaged with the MR scanner 10 such that the member is disposed at least in part in a bore 12 of the scanner 10.

Figure 7:
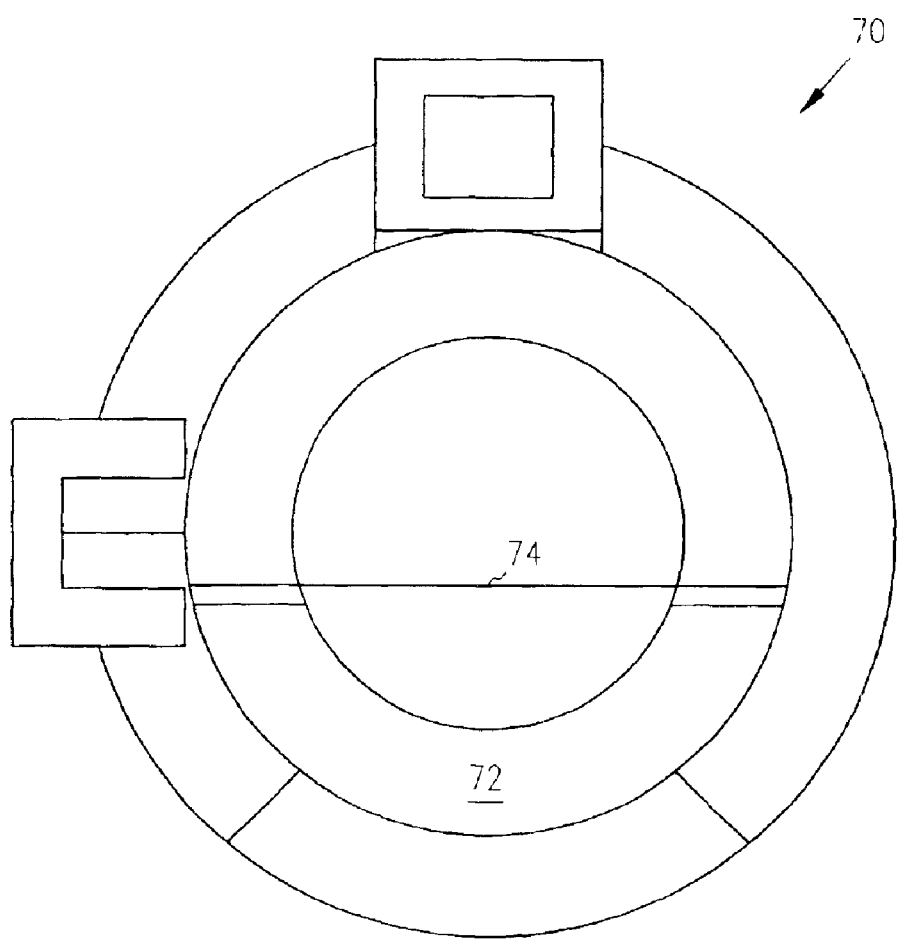
FIG. 7 illustrates a modification to an existing scanner design.

According to yet another example embodiment illustrated in FIG. 7, the present invention provides a modification to the Philips ACS-NT brand (or its successor Intera) MR scanner 70. As shown in FIG. 7, this embodiment of the invention provides for removing the factory apparatus disposed in the lower half of the bore underneath the surface supporting the patient. In its place, the present invention, according to one embodiment, provides a mechanism 72 to rotate and cant a member 74 providing a support surface for the patient.

Thus, the various embodiments of the invention as described herein provide for supporting patients in MR scanners for the purpose of MR imaging and performance of medical procedures in conjunction with MR scanning.

Figure 8:
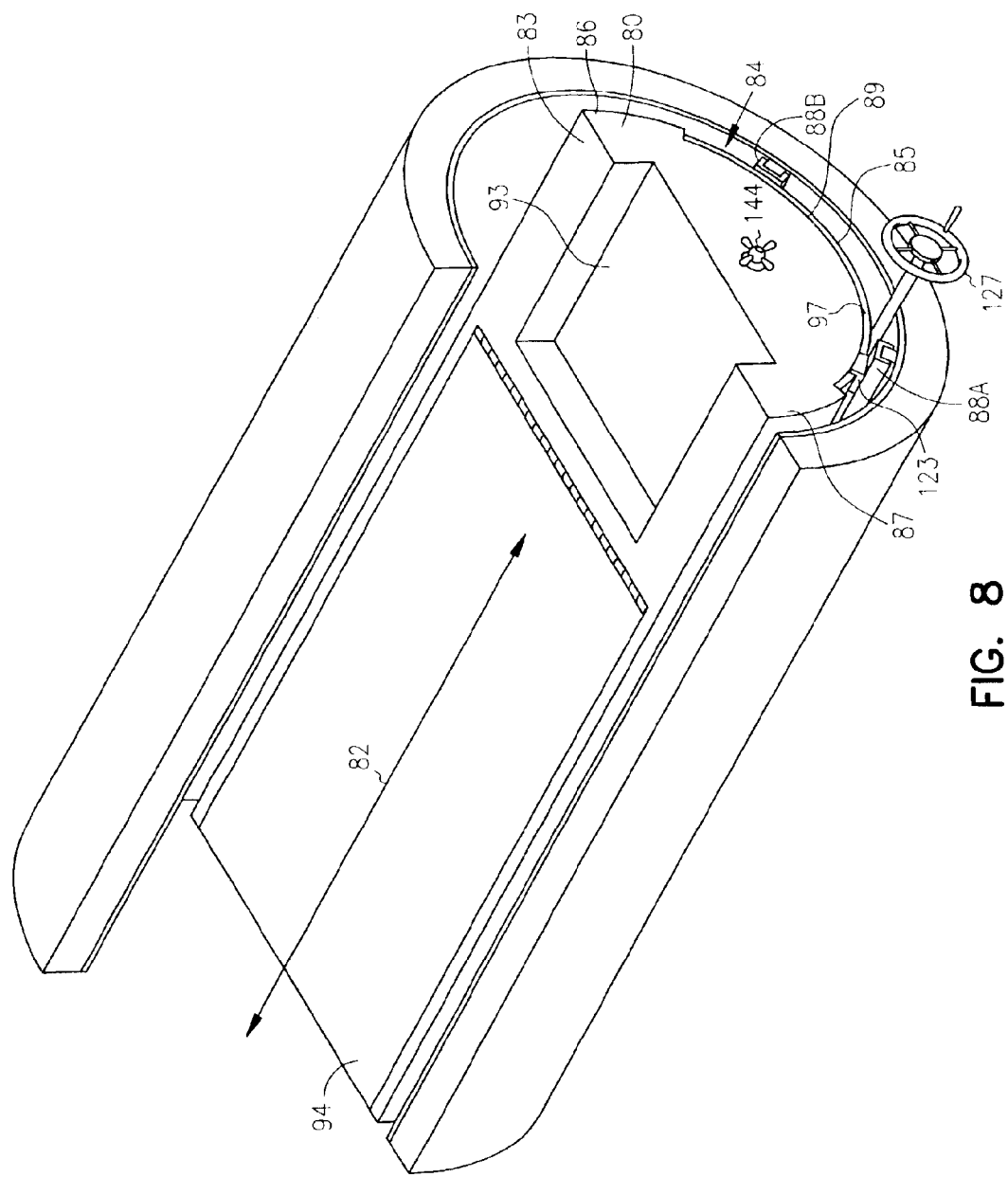
FIG. 8 illustrates yet another embodiment of a method and apparatus according to the present invention wherein channels are attached to the table member and tracks are attached to the bore.
Figure 9:
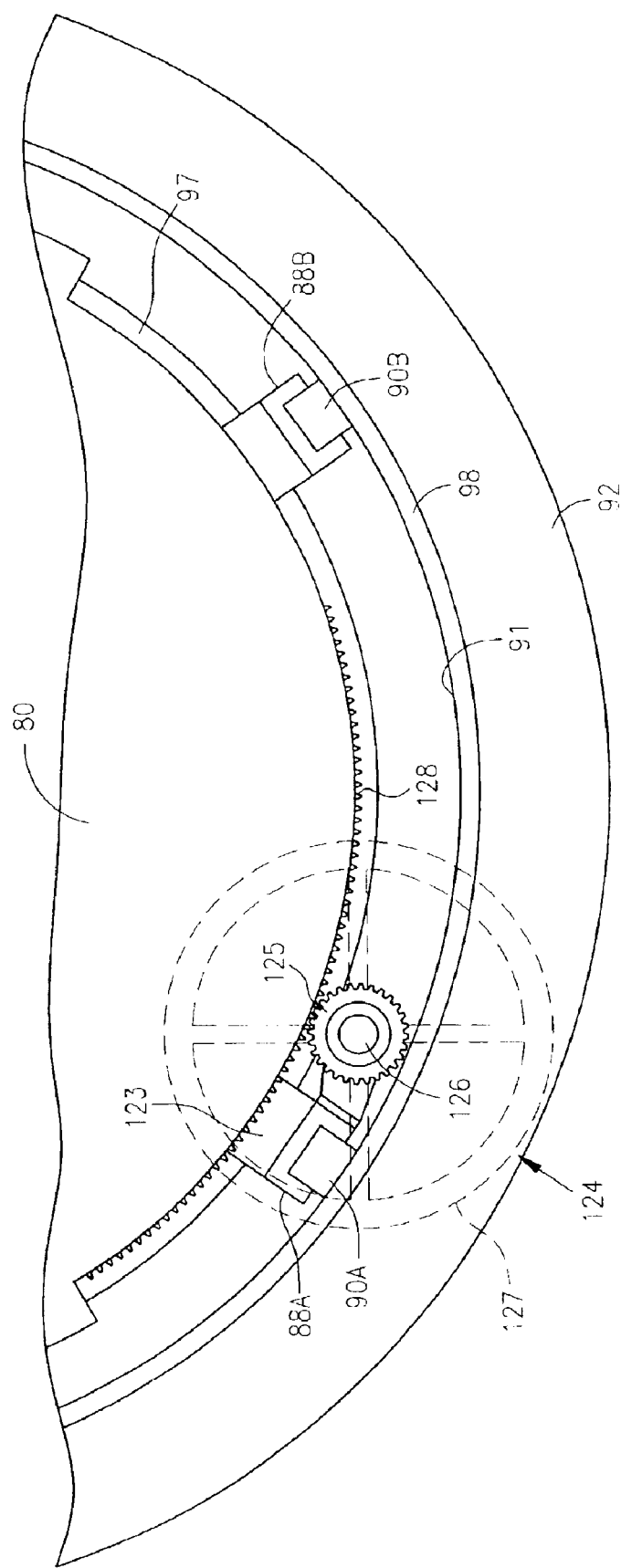
FIG. 9 illustrates yet another embodiment of a method and apparatus according to the present invention wherein gear members are attached to the table member.

Referring now to FIGS. 8 and 9 there is illustrated an embodiment of an apparatus according to the present invention wherein a table 80 for supporting a patient's body has a longitudinal axis 82, a main body portion generally designated as 83, and a recess 84 on its underside 85 that, in one embodiment, runs from a first end 86 to an opposite end 87. Supported in the recess 84 along the bottom of the table 80 are a pair of u-channel rail-engaging members 88A and 88B, therein the open side of the u-channel opens downwardly and points away from the bottom surface of the table 80. Members 88A and 88B are fastened to a downward facing surface 89 through a plurality of short u-channel members 123 that ride in cooperative transverse rail members 97 that extend along surface 89 transverse to the longitudinal axis 82. As illustrated further below with respect to FIG. 12, u-channel members 123 and rails 97 allow table 80 to rotate with respect to the longitudinal axis 82.

As illustrated in FIG. 9, longitudinally extending rail members 90A and 90B are supported above a bottom surface 91 of the bore 92 of MR scanner, for example on a bore lining member 98. Rail members 90A and 90B run along the bottom of bore 92 from substantially one end to another, in one example embodiment. U-channel members 88A and 88B cooperatively engage rail members 90A and 90B, so that the table may be moved and supported within the bore 92 in a longitudinal direction parallel to the longitudinal axis of the bore 92.

Figure 11:
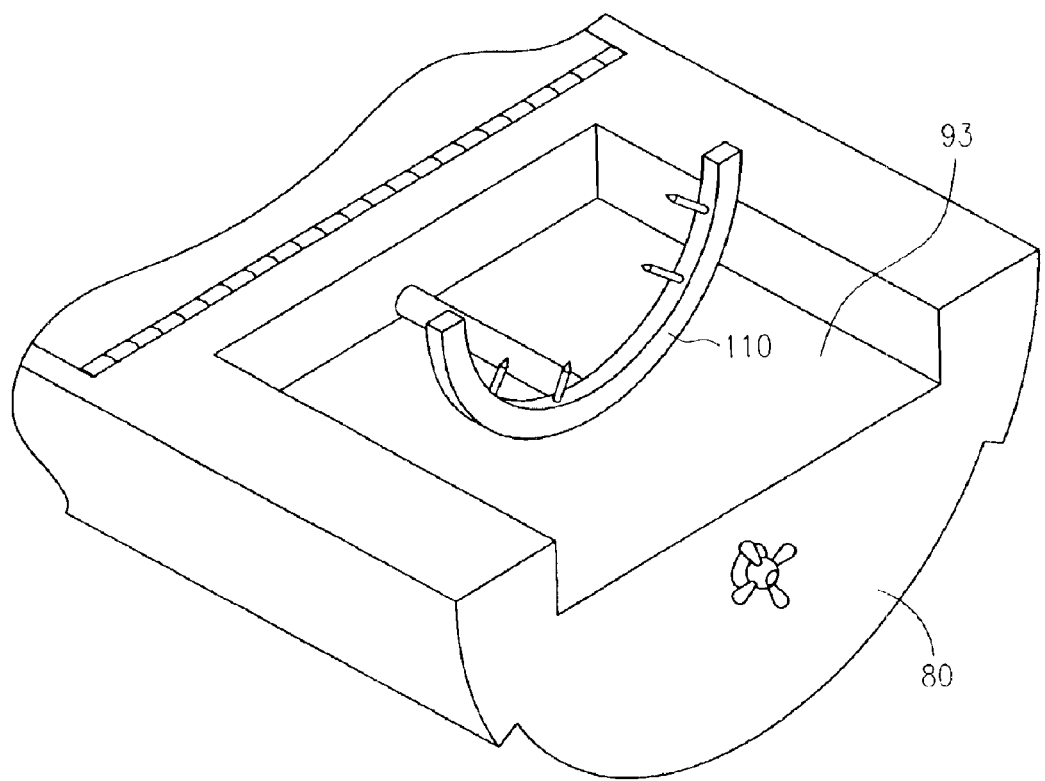
FIG. 11 illustrates yet another embodiment of a method and apparatus according to the present invention wherein a head holder is attached within a recess.

As further illustrated in FIGS. 8 and 9, table 80 includes a of recess 93 on one end substantially underneath the position of a patient's head and neck when lying on the table 80, and optionally includes a surgical head-holder 110, for example as shown in FIG. 11 or as illustrated in FIG. 3 (holder 34), for supporting the patient's head above or within the recess 93.

Figure 10A:
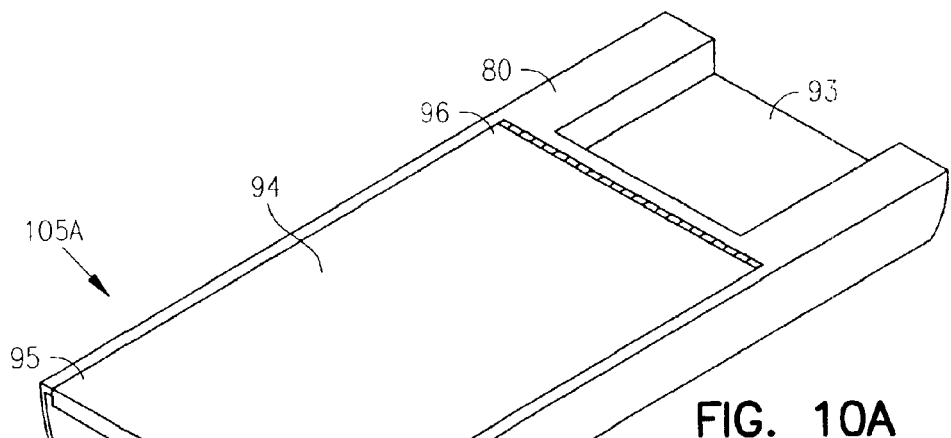
FIGS. 10A, 10B and 10C illustrate yet another embodiment of a method and apparatus according to the present invention wherein piston members are attached to supporting member.
Figure 10B:
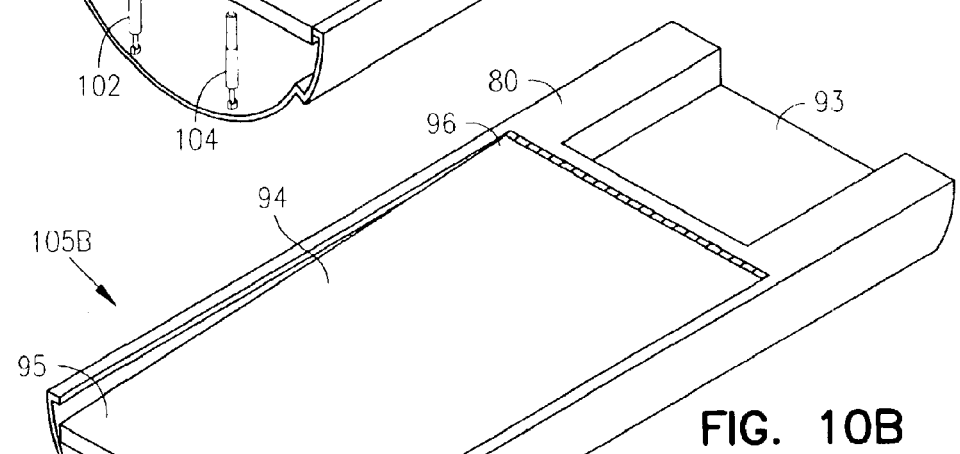
Figure 10C:
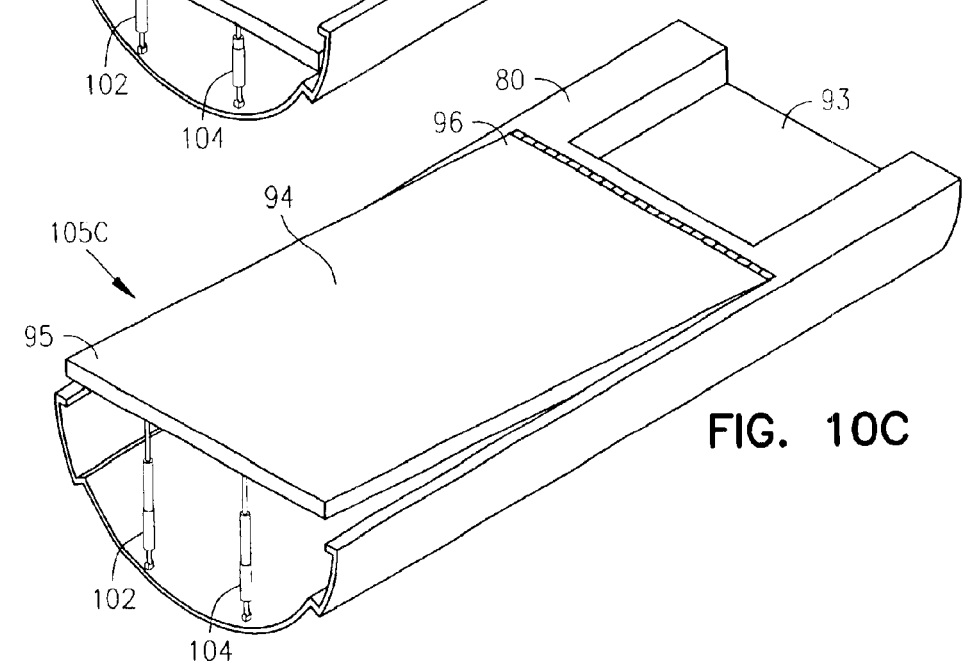

Table 80 further includes a body supporting member 94 that is substantially planar on its top side. As shown in FIGS. 10A, 10B and 10C, table 80 is configured to provide a space below member 94 to allow a distal end 95 to be raised and lowered, with the member 94 pivoting about the opposite end 96, which is positioned proximate the recess 93. In one embodiment, a pair of piston members 102 and 104 are used to raise and lower the body supporting member 94. As shown in FIGS. 10A, 10B and 10C, the member 94 may be moved from a neutral position 105A, a lowered position 105B, or a raised position 105C, and positions between those positions. Accordingly the patient's lower body may be raised up and down in the bore of the MRI scanner.

Figure 12:
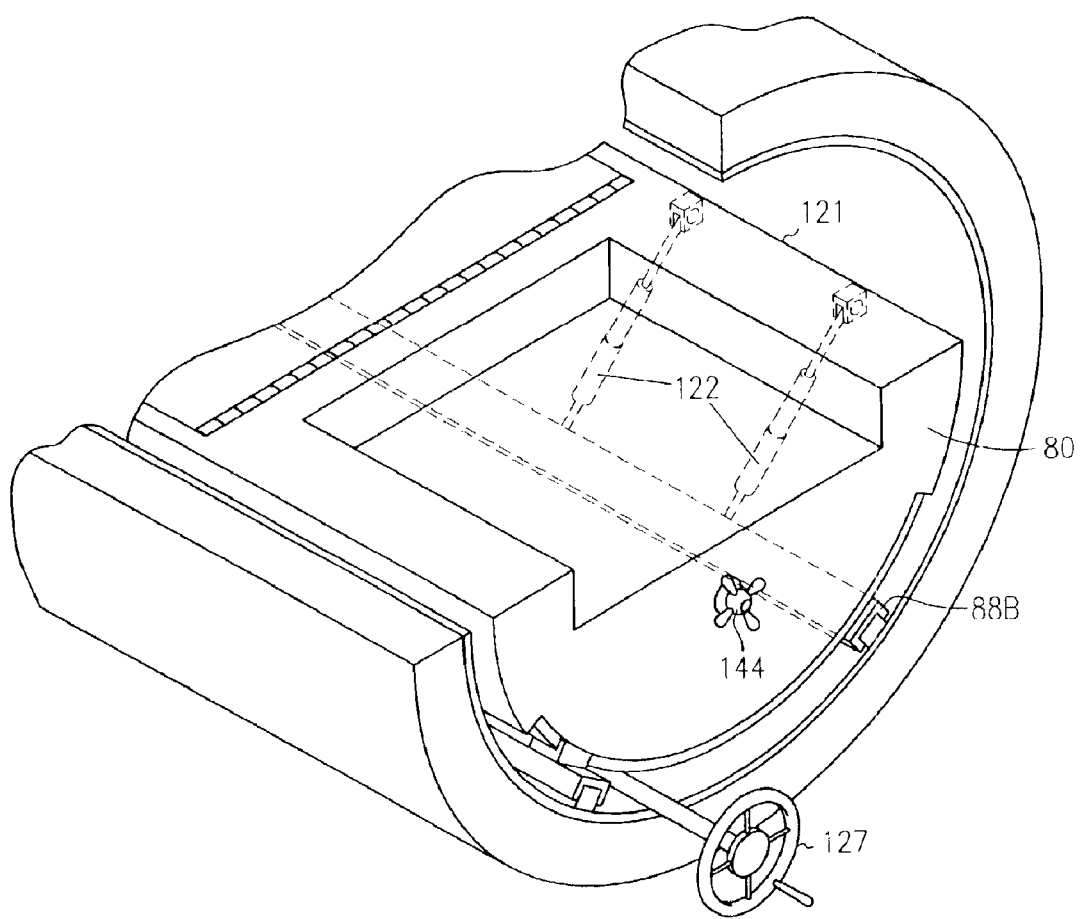
FIG. 12 illustrates yet another embodiment of a method and apparatus according to the present invention wherein piston member are attached to a table member.

Referring now to FIG. 12, there is illustrated apparatus for rotating the table 80 about its longitudinal axis. A plurality of piston members 122 are fastened on one end to the u-channel members 88B (and 88A not shown) and on the other end to a point on the table structure transversely spaced from the channel members and, in one embodiment, near an outer edge 121 of the table 80. Table 80 further includes a geared assembly 124 (shown in FIG. 9) which includes a circular gear member 125 mounted for rotational movement on an axle member 126 having a cranking member 127. A further curvilinear gear member 128 following the contour of the bottom surface of the table 80 is mounted on at least one of the u-channel members 88A and/or 88B. When handle member 127 is rotated it in turn rotates circular gear member 125, which engages gear member 128 and thus causing the table 80 to rotate about its longitudinal axis.

Figure 13:
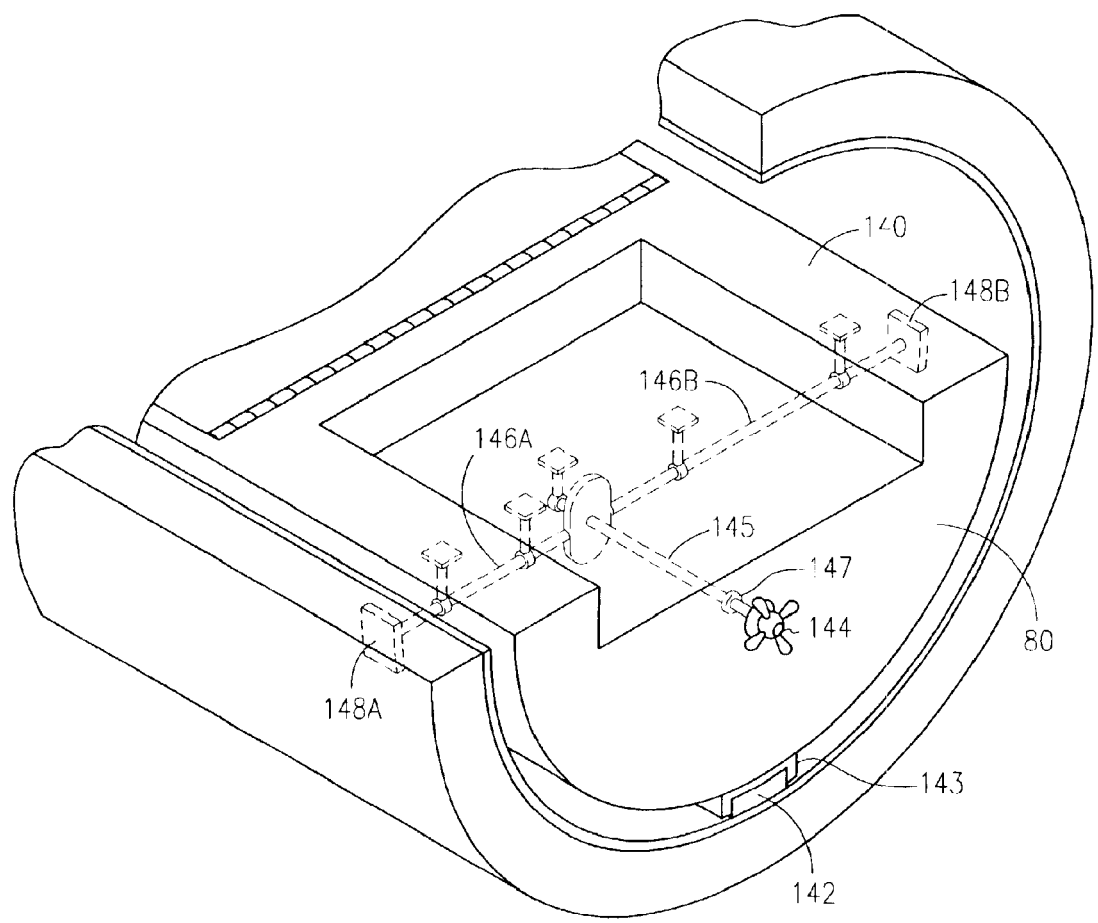
FIG. 13 illustrates yet another embodiment of a method and apparatus according to the present invention wherein brake-pad members are attached to an activation handle for engagement with the side of the bore.

According to another alternate embodiment, as illustrated in FIG. 13, the apparatus is constructed with single rail 142 and u-channel 143, wherein the rail and cooperative u-channel have a substantial width so as to provide sufficient support for the table in the MRI scanner bore. In this embodiment, a single cranking member 144 is provided to move piston members 146A and 146B, and is connected with a push-pull linking member 145 that provides for pushing/pulling on the ends of piston members 146A and 146B. FIG. 13 further illustrates a locking mechanism 147 that provides brake-pad members 148A and 148B on each side of the table 140, and an activation handle that when activated causes the brake pads to engage the side of the bore and therefore keep the table 80 stabilized in the bore.

Figure 14:
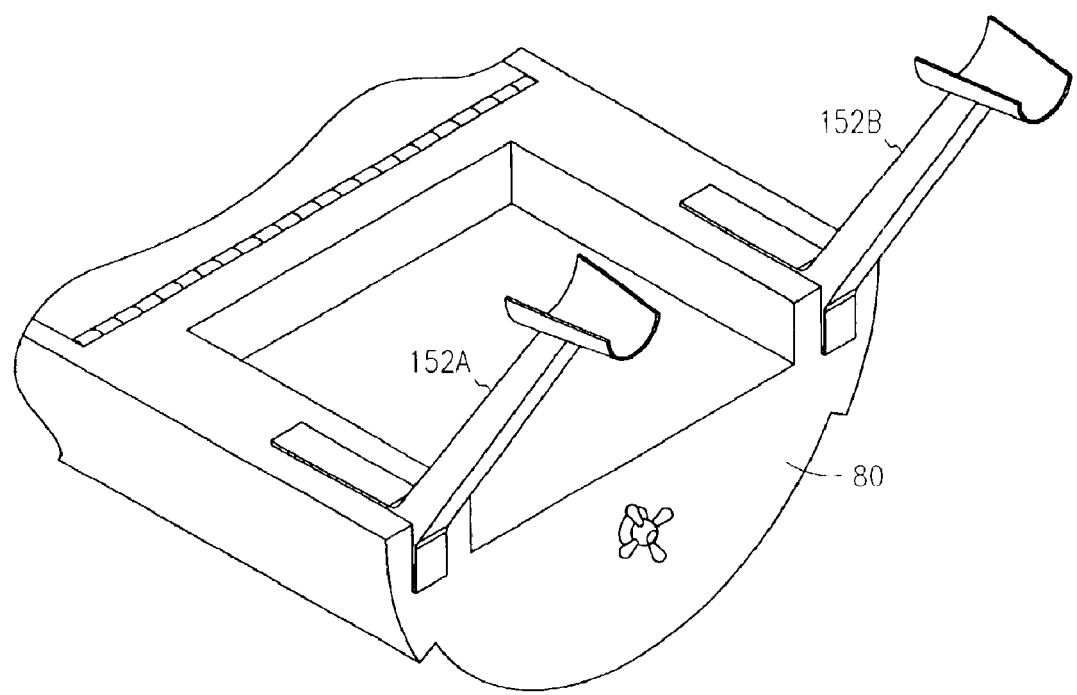
FIG. 14 illustrates yet another embodiment of a method and apparatus according to the present invention wherein stirrup members are attached to a table member.

Referring now to FIG. 14, there is illustrated stirrup members 152A and 152B shown mounted on the end of a table member 80, to receive the foot of a patient lying on the table 80.

Figure 15:
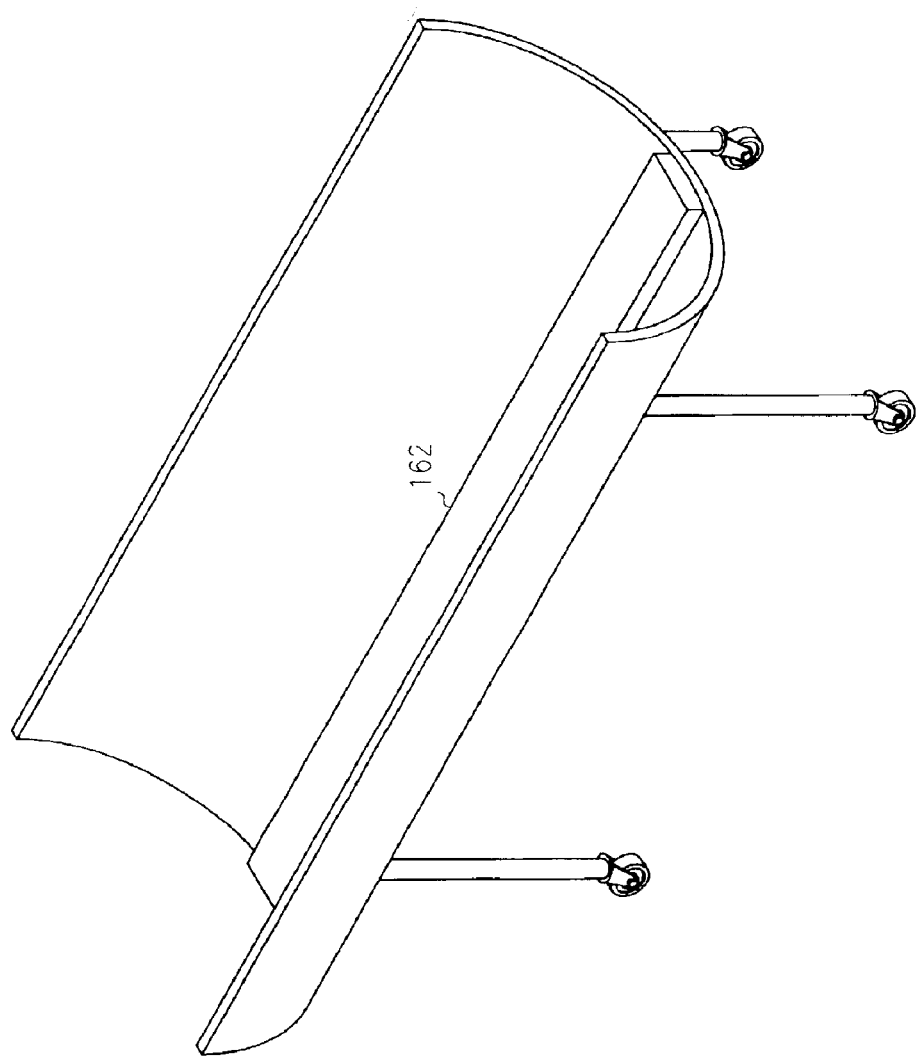
FIG. 15 illustrates yet another embodiment of a method and apparatus according to the present invention wherein a gurney is provided for holding a removable table member.

Referring to FIG. 15, there is illustrated one example embodiment of a gurney with a rail member 162 that is sized, in this example, to receive the u-channel member, for example, from table 140, shown in FIG. 13. This gurney therefore allows table 140 to be supported thereon and when the gurney is positioned aligned longitudinally with the end of the bore of the MRI scanner, allowing the table to be moved into and out of the bore by sliding the table from the rail 162 onto the rail 142, shown in FIG. 13. In the case of more than one rail and u-channel, for example as shown with respect to FIGS. 8 and 9, a gurney is provided with corresponding multiple rails corresponding to the rails in the MR scanner.

Using the above described example embodiments of the tables of the invention, the patient can, for example, be placed on the gurney outside the MR scanner, placed into the bore of the MR scanner for imaging, and then pulled out partially or fully to allow for procedures to be performed.

While in the scanner, the patient's body may be rotated about the longitudinal axis of the scanner on the table as it rotates under the direction of the attending personnel, and/or the patient's body may be tilted up or down on the moveable body supporting member as illustrated with respect to FIGS. 8–10A, B, and C.

According to one example embodiment, member 80 is thus positioned inside the bore 12 of MR scanner 10 so that at least a portion of the patient's body is inside the bore 12. The member 80 is rotated about its longitudinal axis while the member 80 is inside the bore 12, so that the patient's body is rotated about the body's longitudinal axis while in the bore 12 of the MR scanner 10. Thus, according to this embodiment, the member is supported in the bore 12 on a mechanism that supports the member 80 for rotation about the longitudinal axis. Such support may be provided on the edges of the member 80 or along one or more points across the center. Further, the member 80 is freely detachable from the mechanism and removable from the bore 12, for example onto a wheeled gurney, and example embodiment of which is described hereinabove.

Further according to the above-described embodiments, a patient's body is supported on a table member with a substantially planar surface, the table member having a longitudinal axis and a recess on one end substantially underneath a patient's head and neck when lying on the table, and including a surgical head-holder supporting the patient's head above or within the recess. The table is positioned inside a bore of a MR scanner so that at least a portion of the patient's body is inside the bore. The member is freely detachable from the mechanism and removable from the bore.

In yet another example use of the tables hereinabove described, a patient's body 44, shown in FIG. 4, is supported on the table member 40 positioned inside a bore 12 of a MR scanner 10 so that at least a portion of the patient's body 44 is inside the bore 12. The member 40 is canted about a point along its longitudinal axis 42 while the table 40 is inside the bore 12, so that the head or feet of a patient 44 may be raised or lowered with respect to one another while in the bore 12 of the MR scanner 10. According to one example embodiment, the member 40 is supported in the bore 12 on a mechanism that supports the member 40 for canting. The member may be canted using a hydraulically driven component. Further, according to one embodiment, the member 40 is freely detachable from the mechanism and removable from the bore 12.

In yet another embodiment of a method and apparatus according to the present invention shown in FIGS. 6A and 6B, two or more different table members (insertable in bore 12) designed as described above are provided and kept for supporting a patient's body during a medical procedure conducted in conjunction with an MR scanner 10, wherein each member (i.e., 61 and 62) is adapted to be detachably inserted into a bore 12 of the MR scanner 10, and wherein each member provides for a different patient support functionality. One of the different members is selected for use in a medical procedure. The patient's body is positioned on the selected member, and the member is engaged with the MR scanner 10 such that the member is disposed at least in part in a bore 12 of the scanner 10.

According to yet another example embodiment the rails in the MR scanner are provided as modifications to the Philips ACS-NT brand (or its successor Intera) MR scanner. This embodiment of the invention provides for removing the factory apparatus disposed in the lower half of the bore underneath the surface supporting the patient.

What is claimed is:

1. A method, comprising:

supporting a patient's body on an elongate member with a substantially planar surface, the elongate member having a longitudinal axis;

positioning the member inside a bore of a MR scanner so that at least a portion of the patient's body is inside the bore; and rotating the member about its longitudinal axis while the member is inside the bore, so that the patient's body is rotated about the body's longitudinal axis while in the bore of the MR scanner.

2. The method according to claim 1 wherein the member is supported in the bore on a mechanism that supports the member for rotation about the longitudinal axis.

3. The method according to claim 2 wherein the member is freely detachable from the mechanism and removed from the bore.

4. Apparatus, comprising:

an elongate member with a substantially planar surface supporting a patient's body, the elongate member having a longitudinal axis;

a mechanism inside a bore of a MR scanner adapted to support and rotate the member about its longitudinal axis, so that the patient's body is rotated about the body's longitudinal axis while in the bore of the MR scanner.

5. Apparatus according to claim 4 wherein the member is freely detachable from the mechanism.

6. A method, comprising:

supporting a patient's body on an elongate member with a substantially planar surface, the elongate member having a longitudinal axis;

positioning the member inside a bore of a MR scanner so that at least a portion of the patient's body is inside the bore; and rotating the member about its longitudinal axis while the member is inside the bore, so that the patient's body is rotated about the body's longitudinal axis while in the bore of the MR scanner, wherein the member is rotated with a gear coupled to the member.

7. An apparatus, comprising:

an elongate member with a substantially planar surface supporting a patient's body, the elongate member having a longitudinal axis;

a mechanism inside a bore of a MR scanner adapted to support and rotate the member about its longitudinal axis, so that the patient's body is rotated about the body's longitudinal axis while in the bore of the MR scanner, wherein the mechanism includes a gear coupled to the member and operable to rotate the member.

* * * * *